United States Patent [19]

Marx et al.

[11] 3,996,358

[45] Dec. 7, 1976

[54] 21-ESTERS OF STEROIDAL-21-ALDEHYDE HYDRATES AND 21-ALDEHYDE HEMIACETALS AND METHODS OF PREPARATION

[75] Inventors: Michael Marx, Sunnyvale; Denis John Kertesz, Menlo Park, both of Calif.

[73] Assignee: Syntex (U.S.A.) Inc., Palo Alto, Calif.

[22] Filed: July 7, 1975

[21] Appl. No.: 593,578

[52] U.S. Cl. .................. 424/241; 260/239.55 D; 260/397.45
[51] Int. Cl.² .......................................... C07J 5/00
[58] Field of Search ............ 260/239.55 D, 397.45

[56] References Cited

UNITED STATES PATENTS

| | | | |
|---|---|---|---|
| 3,519,659 | 7/1970 | Schmidlin et al. | 260/397.45 |
| 3,733,318 | 5/1973 | Marx et al. | 260/397.45 |

*Primary Examiner*—Elbert L. Roberts
*Attorney, Agent, or Firm*—Alan M. Krubiner; William B. Walker; Natalie Jensen

[57] ABSTRACT

21-Esters of 21-aldehyde hydrates and 21-aldehyde hemiacetals of steroids of the corticoid series are prepared from the corresponding 21-hydroxy steroids and have utility as antiinflammatory agents.

17 Claims, No Drawings.

21-ESTERS OF STEROIDAL-21-ALDEHYDE HYDRATES AND 21-ALDEHYDE HEMIACETALS AND METHODS OF PREPARATION

SUMMARY

The present invention relates to cyclopentanophenanthrene derivatives and to certain novel compounds obtained as intermediates.

More particularly, the present invention relates to compounds represented by the formula:

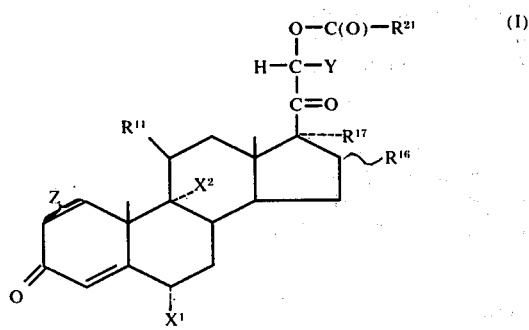

wherein $R^{11}$ is chloro or hydroxy; $R^{16}$ independently is methyl; $R^{17}$ independently is hydroxy or acyloxy having 2 to 8 carbon atoms or $R^{16}$ and $R^{17}$ taken together are 16α,17α-isopropylidenedioxy; $R^{21}$ is hydrogen, lower alkyl having 1 to 8 carbon atoms or phenyl; $X^1$ and $X^2$ are independently hydrogen, chloro or fluoro, with the proviso that when $R^{11}$ is chloro, $X^2$ is chloro; Y is —O—CO(O)—$R^{21}$ or —O$R^{21'}$ in which $R^{21'}$ is lower alkyl having 1 to 8 carbon atoms; and Z is a single or double bond.

Compounds embraced by generic Formula (I) can be represented subgenerically by the following formulas:

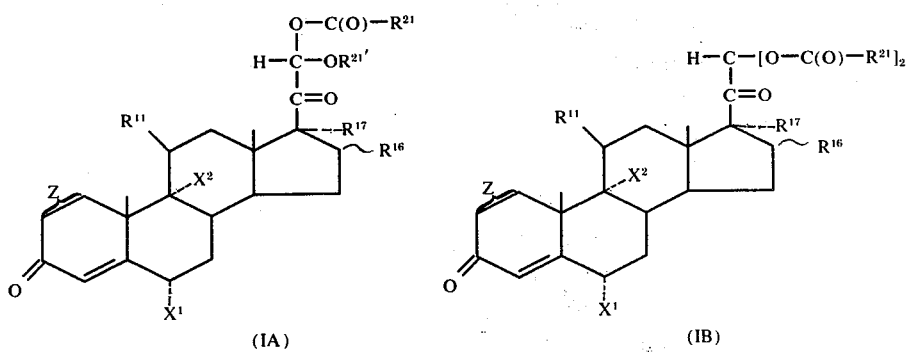

wherein $R^{11}$, $R^{16}$, $R^{17}$, $R^{21}$, $R^{21'}$, Z, $X^1$ and $X^2$ are as previously defined.

Preferred compounds embraced by subgeneric Formula (IA) are those wherein the $R^{21}$ and $R^{21'}$ groups contain a total of 1 to 10 carbon atoms. Particularly preferred compounds are those where the $R^{21}$ and $R^{21'}$ groups contain a total of 1 to 5 carbon atoms.

Preferred compounds embraced by subgeneric Formula (IB) are those wherein the $R^{21}$ group contains 0 to 7 carbon atoms. Particularly preferred compounds are those where the $R^{21}$ group contains 0 to 4 carbon atoms.

The compounds of the instant invention are potent topical anti-inflammatory agents. Although the instant compounds exhibit low systemic activity in the rat as measured in standard assays, e.g. Rat Thymolytic Assay and the Anti-inflammatory Assay Utilizing Carrageenan-induced Rat Paw Edema, they exhibit high topical activity in humans as measured in the Stoughton-McKenzie Assay (Human Vasoconstrictor Assay). In spite of the fact that systemic effects such as adrenal atrophy, mineralocorticoid effects and collagen disorders may be produced by large doses of the instant compounds if administered for long periods of time, the favorable topical/systemic activity ratio of the instant compounds permits the use of such small doses that these systemic effects are minimized. This combination of high topical anti-inflammatory activity coupled with negligible systemic activity renders the instant compounds highly suitable for the alleviation of inflammatory disorders.

The present inventon further relates to a method for treating symptoms associated with inflammatory disorders, which method comprises administering an effective amount of a compound selected from those represented by Formula (I) or a pharmaceutical composition incorporating such a compound as an active ingredient.

The present invention still further relates to pharmaceutical compositions useful for treating inflammatory disorders. These compositions comprise an effective amount of a compound selected from those represented by Formula (I) in admixture with a pharmaceutically acceptable non-toxic carrier.

Suitable carriers or medicament vehicles for topical application of the novel steroids of the instant invention include creams, ointments, lotions, emulsions, solutions, and the like. For example, a suitable ointment for topical application of compounds of the instant invention contains 15 to 45 percent of a saturated fatty alcohol having 16 to 24 atoms such as cetyl alcohol, stearyl alcohol, behenyl alcohol, and the like and 45 to 85 wt. percent of a glycol solvent such as propylene glycol, polyethylene glycol, dipropylene glycol, and the mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide an ester of a fatty acid having from 16 to 24 carbon atoms such as sorbitol monostearate, polyethylene glycol monostearate, polypropylene glycol monostearate, or a corresponding mono-ester of other fatty acids such as oleic acid and palmitic acid; and 0 tp 20 wt. percent of a penetrant such as dimethyl sulfoxide, dimethylacetamide, dimethylformamide, and the like.

The concentration of corticosteroid in pharmaceutical compositions suitable for topical application will vary depending upon the particular activity of the steroid used in conjunction with the condition and subject to be treated. In general, topical preparations containing 0.005 to 1% by weight of the active steroid are advantageously employed.

In the specification and claims the following definitions apply:

The wavy line ( ) used in the depicted formulas indicates that the substituent attached to those positions can be in either the ($\alpha$) or ($\beta$) configuration.

The broken line (---) used in the depicted formulas indicates that the substituent attached to those positions is in the $\alpha$ configuration.

The unbroken line (—) used in the depicted formulas indicates that the substituent attached to those positions is in the $\beta$ configuration.

The term "lower alkyl" defines aliphatic hydrocarbons containing from 1 to 8 carbon atoms including all isomers thereof. Typical lower alkyl groups are methyl, ethyl, n-propyl, isopropyl, n-butyl, sec-butyl, n-amyl, n-hexyl, n-heptyl, n-octyl, and so forth.

The term "acyloxy" refers to those esters employed in the corticosteroid art having from 2 to 8 carbon atoms and being derived from alkanoic or phenyl carboxylic acids. Typical acyloxy groups expressed as the ester include for example acetate, propionate, butyrate, valerate, caproate, enanthate, octanoate, benzoate and the like.

Compounds of Formula (I) wherein Y is not —O—C-(O)—$R^{21}$ exist in two epimeric forms, i.e., the 21(R) and 21(S) forms. Accordingly, all nomenclature, formulas and discussion herein is intended to refer to both forms and mixtures thereof unless otherwise specified.

DETAILED DESCRIPTION

The present invention, in a further aspect, is directed to methods for the preparation of the subject compounds of the instant invention according to the following reaction sequences:

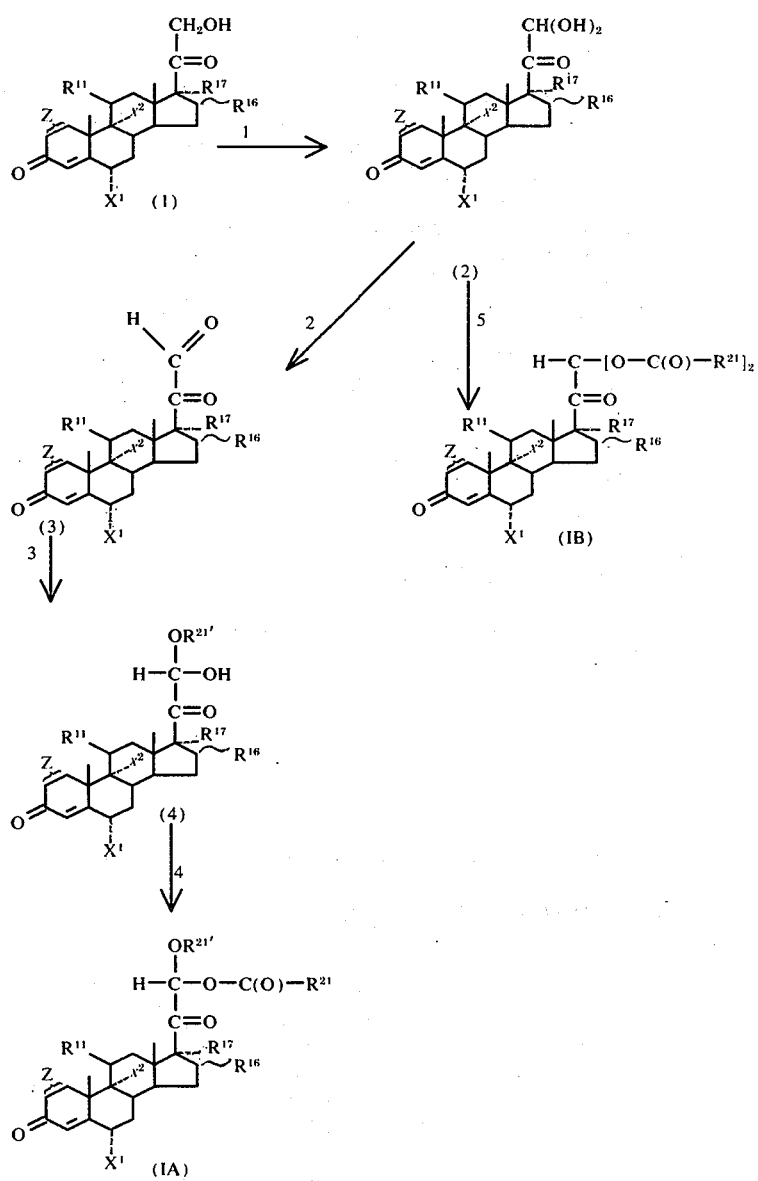

In the above formulas $R^{11}$, $R^{16}$, $R^{17}$, $R^{21}$, $R^{21'}$, $X^1$, $X^2$ and Z are as previously defined.

Compounds of Formula (IA), i.e., the 21-esters of steroidal 21-aldehyde hemiacetals, are prepared via reaction steps 1–4 as follows:

A 21-hydroxy steroid (1) is contacted with air in the presence of a copper (II) catalyst such as cupric acetate to yield the 21-aldehyde hydrate (2). The reaction is preferably conducted in methanol at a temperature of 5° to 30° C. for a period of 30 minutes to 6 hours.

The 21-aldehyde hydrate (2) is then heated at a temperature of 100° to 130° C. for a period of 30 minutes to 3 hours to yield the 21-aldehyde (3) which is then reacted with a lower alkanol containing 1 to 8 carbon atoms at a temperature of 20° to 60° C. for a period of 15 minutes to 1 hour to yield the 21-aldehyde hemiacetal (4).

Reaction of the 21-aldehyde hemiacetal (4) with a suitable acylating agent such as carboxylic acid anhydride or a acyl halide in the presence of an organic base such as triethylamine, pyridine and the like yields the 21-ester of the 21-aldehyde hemiacetal (IA). The reaction is most advantageously conducted utilizing the amine base, preferably pyridine, as the solvent. However, the reaction can also be run in an inert organic solvent such as benzene, methylene chloride and the like. The reaction is carried out for a period of 2 to 24 hours at a temperature of 0° to 20° C.

Compounds of Formula (IB), i.e., the 21,21-diesters of steroidal 21-aldehyde hydrates, are prepared via reaction step 5 as follows:

A 21-aldehyde hydrate (2) is treated with a suitable acylating agent such as an organic anhydride or an acyl halide optionally in the presence of an organic base such as pyridine, triethylamine and the like, to yield the 21,21-diester of the 21-aldehyde hydrate (IB). The reaction is preferably conducted utilizing the ahydride or acyl halide as the solvent and is carried out at a temperature of 50° to 100° C. for a period of 2 to 24 hours.

The 21-hydroxy steroid starting materials (1) used to prepare the subject compounds of the instant invention are available commercially or can be prepared according to known procedures. Information concerning the preparation of 21-hydroxy steroids suitable for use in the preparation of compounds of Formula (I) can be obtained, for example from U.S. Pat. Nos. 3,048,581 and 3,126,375; and from Fried et al., J. Am. Chem. Soc., 802, 338 (1958) and Mills et al., J. Am. Chem. Soc., 82, 3399 (1960). Additional information concerning the preparation of 21-hydroxy steroids suitable for use in the preparation of compounds of Formula (I) can be found for example, in U.S. Pat. Nos. 2,894,963, 3,013,033 and 3,119,748; and Edwards et al., Proc. Chem. Soc. (London), p. 87 (1959), Edwards et al., J. Am. Chem. Soc., 82, 2318 (1960), and Taub et al., J. Am. Chem. Soc., 80, 4435 (1958).

Acylating agents used in the preparation of the subject compounds of the instant invention include carboxylic acid anhydrides and acyl halides. Examples of suitable anhydrides include acetic-formic anhydride, acetic anhydride propionic anhydride, butyric anhydride, benzoic anhydride and the like. Examples of suitable acyl halides include acetyl chloride propionyl chloride, butyroyl cloride, n-valeryl chloride, isovaleryl chloride, n-hexanoyl chloride, n-heptanoyl chloride, n-octanoyl chloride and the like and the corresponding acyl bromides.

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

Example 1

To a slurry of 12.0 g. of 6α,9α-difluoro-11β,17α,17α,21-tetrahydroxypregna-1,4-diene-3,20-dione-16,17-acetonide in 130 ml. of dry methanol is added a solution of 0.68 g. of cupric acetate hydrate in 40 ml. methanol. Air is then sparged through the mixture for 2 hours. Thereafter, the mixture is evaporated to dryness and the residue is taken up in ethyl acetate and washed with water and then with a dilute aqueous solution of potassium bicarbonate and then again with water. The solution is evaporated to dryness and the resulting residue is then dissolved in acetone. The acetone solution is diluted with a substantial volume of water whereupon the resulting precipitate is filtered and dried under vacuum to yield 6α,9α-difluoro-11β,16α,17α,21,21-pentahydroxypregna-1,4-diene-3,20-dione-16,17-acetonide.

Example 2

6α,9α-difluoro-11β,16α,17α,21,21-pentahydroxypregna-1,4-diene-3,20-dione-16,17-acetonide (4.0 g.) is heated under high vacuum in an oil bath at 100° C. for 1 hour to yield 6α,9α-difluoro-11β,16α,17α-trihydroxypregna-1,4-diene-3,20,21-trione-16,17-acetonide.

Example 3

6α,9α-difluoro-11β,16α,17α-trihydroxypregna-1,4-diene-3,20,21-trione-16,17-acetonide (obtained above in Example 2) is dissolved in 50 ml. of dry methanol. After stirring for approximately 15 minutes at room temperature the solution color changes from yellow to colorless. The solution is then evaporated and dried at 50° C. under vacuum to yield 6α,9α-difluoro-11β,16α,17α,21, 21-pentahydroxypregna-1,4-diene-3,20-dione-16,17-acetonide-21-methyl ether.

Replacing methanol in the above procedure with other alkanols, e.g., ethanol, n-propanol, isopropanol, n-butanol, sec-butanol, amyl alcohol, n-hexanol, n-heptanol and n-octanol, etc., is productive of the corresponding 21-aldehyde hemiacetals, for example, 6α,9α-difluoro-11β,16α,17α,21,21-pentahydroxypregna-1,4-diene-3,20-dione-16,17-acetonide-21-ethyl ether, 6α,9α-difluoro-11β,16α,17α,21,21-pentahydroxypregna-1,4-diene-3,20-dione-16,17-acetonide-21-n-propyl ether, 6α,9α-difluoro-11β,16α,17α,21,21-pentahydroxypregna-1,4-diene-3,20-dione-16,17-acetonide-21-isopropyl ether, 6α,9α-difluoro-11β,16α,17α,21,21-pentahydroxypregna-1,4-diene-3,20-dione-16,17-acetonide-21-n-butyl ether, 6α,9α-difluoro-11β,16α,17α,21,21-pentahydroxypregna-1,4-diene-3,20-dione-16,17-acetonide-21-sec-butyl ether, 6α,9α-difluoro-11β,16α,17α,21,21-pentahydroxypregna-1,4-diene-3,20-dione-16,17-acetonide-21-n-amyl ether, 6α,9α-difluoro-11β,16α,17α,21,21-pentahydroxy-pregna-1,4-diene-3,20-dione-16,17-acetonide-21-n-hexyl ether,
6α,9α-difluoro-11β,16α,17α,21,21-pentahydroxy-pregna-1,4-diene-3,20-dione-16,17-acetonide-21-n-heptyl ether, and
6α,9α-difluoro-11β,16α,17α, 21,21-pentahydroxy-pregna-1,4-diene-3,20-dione-16,17-acetonide-21-n-octyl ether.

Example 4

I. 1 g. of 6α,9α-difluoro-11β,16α,17α,21,21-pentahydroxypregna-1,4-diene-3,20-dione-16,17-acetonide-21-methyl ether is added an ice-cooled mixture of 8 ml. of pyridine and 2 ml. acetic anhydride. The resulting solution is stirred at 0° C. for a period of 18 hours. Thereafter, the reaction mixture is poured into ice water and the solid which forms is collected by filtration, washed with water until neutral and vacuum dried at 80° C. to yield 6α,9α-difluoro-11β,16α,17α,21,21-pentahydroxypregna-1,4-diene-3,20-dione-16,17-acetonide-21-acetate-21-methyl ether, m.p. 130°–135° C.

Similarly, repeating the above procedure utilizing other appropriate acylating agents is productive of the following 6α,9α-difluoro-11β,16α,17α,21,21-pentahydroxypregna-1,4-diene-3,20-dione-16,17-acetonide-21-acyloxy-21-methyl ethers:

6α,9α-difluoro-11β,16α,17α,21,21-pentahydroxy-pregna-1,4-diene-3,20-dione-16,17-acetonide-21-formate-21-methyl ether,
6α,9α-difluoro-11β,16α,17α,21,21-pentahydroxy-pregna-1,4-diene-3,20-dione-16,17-acetonide-21-propionate-21-methyl ether,
6α,9α-difluoro-11β,16α,17α,21,21-pentahydroxy-pregna-1,4-diene-3,20-dione-16,17-acetonide-21-n-butyrate-21-methyl ether,
6α,9α-difluoro-11β,16α,17α,21,21-pentahydroxy-pregna-1,4-diene-3,20-dione-16,17-acetonide-21-n-valerate-21-methyl ether,
6α,9α-difluoro-11β,16α,17α,21,21-pentahydroxy-pregna-1,4-diene-3,20-dione-16,17-acetonide-21-isovalerate-21-methyl ether,
6α,9α-difluoro-11β,16α,17α,21,21-pentahydroxy-pregna-1,4-diene-3,20-dione-16,17-acetonide-21-n-hexanoate-21-methyl ether,
6α,9α-difluoro-11β,16α,17α,21,21-pentahydroxy-pregna-1,4-diene-3,20-dione-16,17-acetonide-21-n-heptanoate-21-methyl ether,
6α,9α-difluoro-11β,16α,17α,21,21-pentahydroxy-pregna-1,4-diene-3,20-dione-16,17-acetonide-21-octanoate-21-methyl ether, and
6α,9α-difluoro-11β,16α,17α,21,21-pentahydroxy-pregna-1,4-diene-3,20-dione-16,17-acetonide-21-benzoate-21-methyl ether.

In like manner, repeating the above procedure utilizing other 6α,9α-difluoro-11β,16α,17α,21,21-pentahydroxypregna-1,4-diene-3,20-dione-16,17-acetonide-21-alkyl ethers in combination with appropriate acylating agents is productive of the following 6α,9α-difluoro-11β,16α,17α,21,21-pentahydroxypregna-1,4-diene-3,20-dione-16,17-acetonide-21-acyloxy-21-alkyl ethers:

6α,9α-difluoro-11β,16α,17α,21,21-pentahydroxy-pregna-1,4-diene-3,20-dione-16,17-acetonide-21-formate-21-ethyl ether,
6α,9α-difluoro-11β,16α,17α,21,21-pentahydroxy-pregna-1,4-diene-3,20-dione-16,17-acetonide-21-acetate-21-ethyl ether,
6α,9α-difluoro-11β,16α,17α,21,21-pentahydroxy-pregna-1,4-diene-3,20-dione-16,17-acetonide-21-propionate-21-ethyl ether,
6α,9α-difluoro-11β,16α,17α,21,21-pentahydroxy-pregna-1,4-diene-3,20-dione-16,17-acetonide-21-n-butyrate-21-ethyl ether,
6α,9α-difluoro-11β,16α,17α,21,21-pentahydroxy-pregna-1,4-diene-3,20-dione-16,17-acetonide-21-formate-21-n-propyl ether,
6α,9α-difluoro-11β,16α,17α,21,21-pentahydroxy-pregna-1,4-diene-3,20-dione-16,17-acetonide-21-acetate-21-n-propyl ether,
6α,9α-difluoro-11β,16α,17α,21,21-pentahydroxy-pregna-1,4-diene-3,20-dione-16,17-acetonide-21-propionate-21-n-propyl ether,
6α,9α-difluoro-11β,16α,17α,21,21-pentahydroxy-pregna-1,4-diene-3,20-dione-16,17-acetonide-21-formate-21-isopropyl ether,
6α,9α-difluoro-11β,16α,17α,21,21-pentahydroxy-pregna-1,4-diene-3,20-dione-16,17-acetonide-21-acetate-21-isopropyl ether,
6α,9α-difluoro-11β,16α,17α,21,21-pentahydroxy-pregna-1,4-diene-3,20-dione-16,17-acetonide-21-propionate-21-isopropyl ether,
6α,9α-difluoro-11β,16α,17α,21,21-pentahydroxy-pregna-1,4-diene-3,20-dione-16,17-acetonide-21-formate-21-n-butyl ether,
6α,9α-difluoro-11β,16α,17α,21,21-pentahydroxy-pregna-1,4-diene-3,20-dione-16,17-acetonide-21-acetate-21-n-butyl ether,
6α,9α-difluoro-11β,16α,17α,21,21-pentahydroxy-pregna-1,4-diene-3,20-dione-16,17-acetonide-21-formate-21-sec-butyl ether,
6α,9α-difluoro-11β,16α,17α,21,21-pentahydroxy-pregna-1,4-diene-3,20-dione-16,17-acetonide-21-acetate-21-sec-butyl ether,
6α,9α-difluoro-11β, 16α,17α,21,21-pentahydroxy-pregna-1,4-diene-3,20-dione-16,17-acetonide-21-acetate-21-n-amyl ether,
6α,9α-difluoro-11β,16α,17α,21,21-pentahydroxy-pregna-1,4-diene-3,20-dione-16,17-acetonide-21-n-valerate-21-ethyl ether,
6α,9α-difluoro-11β,16α,17α,21,21-pentahydroxy-pregna-1,4-diene-3,20-dione-16,17-acetonide-21-n-heptanoate-21-ethyl ether,
6α,9α-difluoro-11β,16α,17α,21,21-pentahydroxy-pregna-1,4-diene-3,20-dione-16,17-acetonide-21-benzoate-21-ethyl ether,
6α,9α-difluoro-11β,16α,17α,21,21-pentahydroxy-pregna-1,4-diene-3,20-dione-16,17-acetonide-21-n-butyrate-21-n-propyl ether,
6α,9α-difluoro-11β,16α, 17α,21,21-pentahydroxy-pregna-1,4-diene-3,20-dione-16,17-acetonide21-n-hexanoate-21-n-propyl ether,
6α,9α-difluoro-11β,16α,17α,21,21-pentahydroxy-pregna-1,4-diene-3,20-dione-16,17-acetonide-21-n-octanoate-21-n-propyl ether,
6α,9α-difluoro-11β,16α,17α,21,21-pentahydroxy-pregna-1,4-diene-3,20-dione-16,17-acetonide- 21-n-valerate-21-isopropyl ether,
6α,9α-difluoro-11β,16α,17α,21,21-pentahydroxy-pregna-1,4-diene-3,20 -dione-16,17-acetonide-21-n-heptanoate-21-isopropyl ether,
6α,9α-difluoro-11β,16α,17α,21,21-pentahydroxy-pregna-1,4-diene-3,20-dione-16,17-acetonide-21-benzoate-21-isopropyl ether,
6α,9α-difluoro-11β,16α,17α,21,21-pentahydroxy-pregna-1,4-diene-3,20-dione-16,17-acetonide- 21-propionate-21-n-butyl ether, 6α,9α-difluoro-11β, 16α,17α,21,21-pentahydroxypregna-1,4-diene-3,20-dione-16,17-acetonide-21-isovalerate-21-methyl ether, α,9α-difluoro-11β,16α,17α,21,21-pentahydroxypregna-1,4-diene-3,20-dione-16,17-acetonide-21-n-heptanoate-21-n-butyl ether, 6α,9α-difluoro-11β,16α,17α,21,21-pentahydroxypregna-1,4-diene-3,20-dione-16,17-acetonide-21-n-butyrate-21-sec-butyl ether, 6α,9α-difluoro-11β, 16α,17α,21,21-pentahydroxypregna-1,4-diene-3,20-dione-16,17-acetonide-21-n-hexanoate-21-sec-butyl ether, 6α,9α-difluoro-11β, 16α,17α,21,21-pentahydroxypregna-1,4-diene-3,20-dione-16,17-acetonide-21-benzoate-21-sec-butyl ether, 6α, 9α-difluoro-11β,16α,17α,21,21-pentahydroxypregna-1,4-diene-3,20-dione-16,17-acetonide-21-propionate-21-n-amyl ether, 6α,9α-difluoro-11β, 16α,17α,21,21-pentahydroxypregna-1,4-diene-3,20-dione-16,17-acetonide-21-n-valerate-21-n-amyl ether, 6α,9α-difluoro-11β,16α,17α,21,21-pentahydroxypregna-1,4-diene-3,20-dione-16,17-acetonide-21-formate-21-n-hexyl ether, 6α,9α-difluoro-11β,16α,17α,21,21-pentahydroxypregna-1,4-diene-3,20-dione-16,17-acetonide-21-propionate-21-n-hexyl ether, 6α,9α-difluoro-11β,16α,17α,21,21-pentahydroxypregna-1,4-diene-3,20-dione-16,17-acetonide-21-isovalerate-21-n-hexyl ether, 6α,9α-difluoro-11β,16α,17α,21,21-pentahydroxypregna-1,4-diene-3,20-dione-16,17-acetonide-21-acetate-21-n-heptyl ether, 6α,9α-difluoro-11β, 16α,17α,21,21-pentahydroxypregna-1,4-diene-3,20-dione16,17-acetonide-21-n-butyrate-21-n-heptyl ether, 6α,9α,-difluoro-11β,16α,17α,21,21-pentahydroxypregna-1,4-diene-3,20-dione-16,17-acetonide-21-formate-21-n-octyl ether, 6α,9α-difluoro-11β,16α,17α,21,21-pentahydroxypregna-1,4-diene-3,20-dione-16,17-acetonide-21-propionate-21-n-octyl ether, 6α,9α-difluoro-11β, 16α,17α,21,21-pentahydroxypregna-1,4-diene-3,20-dione-16,17-acetonide-21-n-octanoate-21-n-butyl ether, 6α,9α-difluoro-11β,16α,17α,21,21-pentahydroxypregna-1,4-diene-3,20-dione-16,17-acetonide-21-n-hexanoate-21-n-hexyl ether, 6α,9α-difluoro-11β,16α,17α,21,21-pentahydroxypregna-1,4-diene-3,20-dione-16,17-acetonide-21-n-heptanoate-21-n-heptyl ether, 6α,9α-difluoro-11β, 16α,17α,21,21-pentahydroxypregna-1,4-diene-3,20-dione-16,17-acetonide-21-n-butyrate-21-n-octyl ether, and 6α,9α-difluoro-11β,16α,17α,21,21-pentahydroxypregna-1,4-diene-3,20-dione-16,17-acetonide-21-benzoate-21-n-octyl ether.

EXAMPLE 5

To 1 g. of 6α,9α-difluoro-11β,16α,17α,21,21-pentahydroxypregna-1,4-diene-3,20-dione-16,17-acetonide is added 10 ml. of acetic anhydride. The resulting solution is stirred at 50° C. for 16 hours. Thereafter, the reaction mixture is poured into ice water and the solid which forms is collected by filtration and washed with water until neutral. The resulting residue is chromatographed on a silica gel column and eluted with 50% ethyl acetate in benzene to yield 6α,9α-difluoro-11β,16α,17α,21,21-pentahydroxypregna-1,4-diene-3,20-dione-16,17-acetonide-21,21-diacetate, m.p. 137°–143° C.

Similarly, repeating the above procedure utilizing other appropriate acylating agents is productive of the following 6α,9α-difluoro-11β, 16α,17α,21,21-pentahydroxypregna-1,4-diene-3,20-dione-16,17-acetonide-21,21-diesters:

6α,9α-difluoro-11β, 16α,17α,21,21-pentahydroxypregna-1,4-diene-3,20-dione-16,17-acetonide-21,21-diformate, 6α,9α-difluoro-11β,16α,17α,21,21-pentahydroxypregna-1,4-diene-3,20-dione-16,17-acetonide-21,21-dipropionate, 6α,9α-difluoro-11β,16α,17α,21,21-pentahydroxypregna-1,4-diene-3,20-dione-16,17-acetonide-21,21-di-n-butyrate, 6α,9α-difluoro-11β,16α,17α,21,21-pentahydroxypregna-1,4-diene-3,20-dione-16,17-acetonide-21,21-di-n-valerate, 6α,9α-difluoro-11β,16α,17α,21,21-pentahydroxypregna-1,4-diene-3,20-dione-16,17-acetonide-21,21-di-isovalerate, 6α,9α-difluoro-11β,16α,17α,21,21-pentahydroxypregna-1,4-diene-3,20-dione-16,17-acetonide-21,21-di-n-hexanoate, 6α,9α-difluoro-11β,16α,17α,21,21-pentahydroxypregna-1,4-diene-3,20-dione-16,17-acetonide-21,21-di-n-heptanoate, 6α,9α-difluoro-11β,16α,17α,21,21-pentahydroxypregna-1,4-diene-3,20-dione-16,17-acetonide-21,21-di-n-octanoate, and 6α,9α-difluoro-11β, 16α,17α,21,21-pentahydroxypregna-1,4-diene-3,20-dione-16,17-acetonide-21,21-dibenzoate.

EXAMPLE 6

In similar manner to the procedures of Examples 1–4, using reactants as dictated by the particular steroid 21-ester desired, the following compounds are prepared:

6α-fluoro-11β,16α,17α,21,21-pentahydroxypregna-1,4-diene-3,20-dione-16,17-acetonide-21-formate-21-methyl ether, 6α-fluoro-11β,16α,17α,21,21-pentahydroxypregna-1,4-diene-3,20-dione-16,17-acetonide-21-acetate-21-isopropyl ether, 6α-fluoro-11β,16α,17α,21,21-pentahydroxypregna-1,4-diene-3,20-dione-16,17-acetonide-21-n-hexanoate-21-methyl ether, 6α-fluoro-11β,16α, 17α,21,21-pentahydroxypregna-1,4-diene-3,20-dione-16,17-acetonide-21-propionate-21-sec-butyl ether, 6α-fluoro-11β,16α,17α,21,21-pentahydroxypregna-1,4-diene-3,20-dione-16,17-acetonide-21-n-octanoate-21-n-heptyl ether, 6α,9α-difluoro-11β,16α,17α,21,21-pentahydroxypregn-4-ene-3,20-dione-16,17-acetonide-21-acetate-21-n-butyl ether, 6α,9α-difluoro-11β, 16α, 17α,21,21-pentahydroxypregn-4-ene-3,20-dione-16,17-acetonide-21-propionate-21-isopropyl ether, 6α,9α-difluoro-11β, 16α,17α,21,21-pentahydroxypregn-4-ene-3,20-dione-16,17-acetonide-21-n-valerate-21-methyl ether, 6α,9α-difluoro-11β,16α,17α,21,21-pentahydroxypregn-4-ene-3,20-dione-16,17-acetonide-21-n-heptanoate-21-methyl ether, 6α,9α-difluoro-11β,16α,17α,21,21-pentahydroxy-pregn-4-ene-3,20-dione-16,17-acetonide-21-n-butyrate-21-n-heptyl ether, 6α-fluoro-11β, 16α,17α,21,21-pentahydroxypregn-4-ene-3,20-dione-16,17-acetonide-21-formate-21-n-amyl ether, 6α-fluoro-11β, 16α,17α,21,21-pentahydroxypregn-4-ene-3,20-dione- 16,17-acetonide-21-acetate-21-ethyl ether, 6α-fluoro-11β, 16α,17α,21,21-pentahydroxypregn-4-ene-3,20-dione-16,17-acetonide-21-n-butyrate-21-methyl ether, 6α-fluoro-11β, 16α,17α,21,21-pentahydroxypregn-4-ene-3,20-dione-16,17-acetonide-21benzoate-21-n-butyl ether, 6α-fluoro-11β,16α,17α,21,21-pentahydroxypregna-4-ene-3,20-dione-16,17-acetonide-21-n-hexanoate-21-n-octyl ether, 9α,11β-dichloro-6α-fluoro-16α,17α,21,21-tetrahydroxypregna-1,4-diene-3,20-dione-16,17-acetonide-21-acetate-21n-propyl ether, 9α,11β-dichloro-6α-fluoro-16α,17α,21,21-tetrahydroxypregna-1,4-diene-3,20-dione-16,17-acetonide-21-n-butyrate-21-ethyl ether, 9α,11βdichloro-6α-fluoro-16α,17α,21,21-tetrahydroxypregna-1,4-diene-3,20-dione-16,17-acetonide-21-benzoate-21-methyl ether, 9α,11β-dichloro-6α-fluoro-16α,17α,21,21-tetrahydroxypregna-1,4-diene-3,20-dione-16,17-acetonide-21-isovalerate-21-n-hexyl ether, 9α,11β-dichloro-6α-fluoro-16α,17α,21,21-tetrahydoxypregna-1,4-diene-3,20-dione-16,17-acetonide-21-n-heptanoate-21-n-amyl ether, 9α-chloro-6α-fluoro-11β, 16α,17α,21,21-pentahydroxypregna-1,4-diene-3,20-dione-16,17-acetonide-21-acetate-21-sec-butyl ether, 9α-chloro-6α-fluoro-11β, 16α,17α,21,21-pentahydroxypregna-1,4-diene-3,20-dione-16,17-acetonide-21-n-valerate-21-methyl ether, 9α-chloro-6α-fluoro-11β,16α,17α,21,21-pentahydroxypregna-1,4-diene-3,20-dione-16,17-acetonide-21-propionate-21-n-propyl ether, 9α-chloro-6α-fluoro-11β,16α,17α,21,21-pentahydroxypregna-1,4-diene-3,20-dione-16,17-acetonide-21-n-heptanoate-21-n-butyl ether, 9α-chloro-6α-fluoro-11β,16α,17α,21,21-pentahydroxypregna-1,4-diene-3,20-dione-16,17-acetonide-21-benzoate-21-n-octyl ether, 6α,9α-difluoro-11β, 16α,17α,21,21-tetrahydroxy-16α-methylpregna-1,4-diene-3,20-dione-21-acetate-21-methyl ether, 6α,9α-difluoro-11β,16α,17α,21,21-tetrahydroxy-16α-methylpregna-1,4-diene-3,20-dione-21-n-butyrate-21-ethyl ether, 6α,9α-difluoro-11β, 16α,17α,21,21-tetrahydroxy-16α-methylpregna-1,4-diene-3,20-dione-21-propionate-21-n-octyl ether, 6α,9α-difluoro-11β,17α,21,21-tetrahydroxy-16α-methylpregna-1,4-diene-3,20-dione-21-n-hexanoate-21-sec-butyl ether, 6α,9α-difluoro-11β,17α,21,21-tetrahydroxy-16α-methylpregna-1,4-diene-3,20-dione-21-benzoate-21-n-amyl ether, 6α,9α-difluoro-11β,17α,21,21-tetrahydroxy-16α-methylpregna-1,4-diene-3,20-dione-17-n-octanoate-21-acetate-21-isopropyl ether, 6α,9α-difluoro-11β,17α,21,21-tetrahydroxy-16α-methylpregna-1,4-diene-3,20-dione-17-n-octanoate-21-propionate-21-methyl ether, 6α,9α-difluoro-11β,17α,21,21-tetrahydroxy-16α-methylpegna-1,4-diene-3,20-dione-17-n-octanoate-21-formate-21-sec-butyl ether, 6α,9α-difluoro-11β,17α,21,21-tetrahydroxy-16α-methylpregna-1,4-diene-3,20-dione-17-n-octanoate-21-n-valerate-21-n-amyl ether, 6α,9α-difluoro-11β,17α,21,21-tetrahydroxy-16α-methylpregna-1,4-diene-3,20-dione-17-n-octanoate-21-n-heptanoate-21-n-octyl ether, 6α,9α-difluoro-11β,17α,21,21-tetrahydroxy-16α-methylpregna-1,4-diene-3,20-dione-17-benzoate-21-acetate-21methyl ether, 6α,9α-difluoro-11β,17α,21,21-tetrahydroxy-16α-methylpregna-1,4-diene-3,20-dione-17-benzoate-21-propionate-21-ethyl ether, 6α,9α-difluoro-11β,17α,21,21-tetrahydroxy-16α-methylpregna-1,4-diene-3,20-dione-17-benzoate-21-n-butyrate-21-n-propyl ether, 6α,9α-difluoro-11β,17α,21,21-tetrahydroxy-16α-methylpregna-1,4-diene-3,20-dione-17-benzoate-21-n-hexanoate-21-n-amyl ether, 6α,9α-difluoro-11β,17α,21,21-tetrahydroxy-16α-methylpregna-1,4-diene-3,20-dione-17-benzoate-21-n-valerate-21-ethyl ether, 9α-fluoro-11β,17α,21,21-tetrahydroxy-16β-methylpregna-1,4-diene-3,20-dione-17-n-valerate-21-acetate-21-n-butyl ether, 9αfluoro-11β,17α,21,21-tetrahydroxy-16β-methylpregna-1,4-diene-3,20-dione-17-n-valerate-21-propionate-21-methyl ether, 9α-fluoro-11β, 17α,21,21-tetrahydroxy-16β-methylpregna-1,4-diene-3,20-dione-17,21-di-n-valerate-21-methyl ether, 9α-fluoro-11β,17α,21,21-tetrahydroxy-16β-methylpregna-1,4-diene-3,20-dione-17-n-valerate-21-n-butyrate-21-n-heptyl ether, 9α-fluoro-11β,17α,21,21-tetrahydroxy-16β-methylpregna-1,4-diene-3,20-dione-17-n-valerate-21-n-octanoate-21-methyl ether, 9α-fluoro-11β,17α,21,21-tetrahydroxy-16β-methylpregn-4-ene-3,20-dione-21-acetate-21-n-propyl ether, 9α-fluoro-11β,17α,21,21-tetrahydroxy-16β-methylpregn-4-ene-3,20-dione-21-propionate-21-ethyl ether, 9α-fluoro-11β,17α,21,21-tetrahydroxy-16β-methylpregn-4-ene-3,20-dione-21-propionate-21-n-heptyl ether, 9α-fluoro-11β,17α,21,21-tetrahydroxy-16β-methylpregn-4-ene-3,20-dione-21-n-octanoate-21-n-propyl ether, 9α-fluoro-11β, 17α,21,21-tetrahydroxy-16β-methylpregn-4-ene-3,20-dione-21-n-butyrate-21-n-octyl ether, 9α-fluoro-11β, 16α,17α,21,21-pentahydroxypregna-1,4-diene-3,20-dione-16,17-acetonide-21-acetate-21-sec-butyl ether, 9α-fluoro-11β,16α,17α,21,21-pentahydroxypregna-1,4-diene-3,20-dione-16,17-acetonide-21-propionate-21-isopropyl ether, 9α-fluoro-11β,16α,17α,21,21-pentahydroxypregna-1,4-diene-3,20-dione-16,17-acetonide-21-n-valerate-21-n-amyl ether, 9α-fluoro-11β,16',17α,21,21-pentahydroxypregna-1,4-diene-3,20-dione-16,17-acetonide-21-n-octanoate-21-ethyl ether, 9α-fluoro-11β,16α,17α,21,21-pentahydroxypregna-1,4-diene-3,20-dione-16,17-acetonide-21-benzoate-21-n-hexyl ether, 6α,9α-difluoro-11β,17α,21,21-tetrahydroxy-16α-methylpregna-1,4-diene-3,20-dione-17,21-diacetate-21-ethyl ether, 6α,9α-difluoro-11β,17α,21,21-tetrahydroxy-16α-methylpregna-1,4-diene-3,20-dione-17-acetate-21-propionate-21-n-propyl ether, 6α,9α-difluoro-11β,17α,21,21-tetrahydroxy-16α-methylpregna-1,4-diene-3,20-dione-17-acetate-21-n-butyrate-21-n-hexyl ether, 6α,9α-difluoro-11β,17α,21,21-tetrahydroxy-16α-methylpregna-1,4-diene-3,20-dione-17-acetate-21-n-hexanoate-21-n-propyl ether, 6α,9α-difluoro-11β,17α,21,21-tetrahydroxy-16α-methylpregna-1,4-diene-3,20-dione-17-acetate-21-n-heptanoate-21-n-hexyl ether, 11β,16α,17α,21,21-pentahydroxypregn-4-ene-3,20-dione-16,17-acetonide-21-formate-21-n-propyl ether, 11β,16α,17α,21,21-pentahydroxypregn-4-ene-3,20-dione-16,17-acetonide-21-acetate-21-methyl ether, 11β,16α,17α,21,21-pentahydroxypregn-4-ene-3,20-dione-16,17-acetonide-21-isovalerate-21-methyl ether, 11β,16α,17α,21,21-pentahydroxypregn-4-ene-3,20-dione-16,17-acetonide-21-n-hexanoate-21-n-butyl ether, 11β,16α,17α,21,21-pentahydroxypregn-4-ene-3,20-dione-16,17-acetonide-21-benzoate-21-n-propyl ether, 11β,16α,17α,21,21-pentahydroxypregna-1,4-diene-3,20-dione-16,17-acetonide-21-acetate-21-n-butyl ether, 11β,16α,17α,21,21-pentahydroxypregna-1,4-diene-3,20-dione-16,17-acetonide-21-propionate-21-ethyl ether, 11β,16α,17α,21,21-pentahydroxypregna-1,4-diene-3,20-dione-16,17-acetonide-21-n-heptanoate-21-isopropyl ether, 11β,16α,17α,21,21-pentahydroxypregna-1,4-diene-3,20-dione-16,17-acetonide-21-benzoate-21-methyl ether,

11β,16α,17α,21,21-pentahydroxypregna-1,4-diene-3,20-dione-16,17-acetonide-21-n-valerate-21-n-heptyl ether, 6α-chloro-11β,16α,17α,21,21-pentahydroxypregn-4-ene-3,20-dione-16,17-acetonide-21-acetate-21-methyl ether, 6α-chloro-11β,16α,17α,21,21-pentahydroxypregn-4-ene-3,20-dione-16,17-acetonide-21-propionate-21-isopropyl ether, 6α-chloro-11β,16α,17α,21,21-pentahydroxypregn-4-ene-3,20-dione-16,17-acetonide-21-n-butyrate-21-ethyl ether, 6α-chloro-11β,16α,17α,21,21-pentahydroxypregn-4-ene-3,20-dione-16,17-acetonide-21-n-valerate-21-n-butyl ether, 6α-chloro-11β,16α,17α,21,21-pentahydroxypregn-4-ene-3,20-dione-16,17-acetonide-21-n-octanoate-21-n-heptyl ether,

11β,17α,21,21-tetrahydroxy-16α-methylpregna-1,4-diene-3,20-dione-17-valerate-21-acetate-21-n-propyl ether, 11β,17α,21,21-tetrahydroxy-16α-methylpregna-1,4-diene-3,20-dione-17-valerate-21-n-butyrate-21-methyl ether, 11β,17α,21,21-tetrahydroxy-16α-methylpregna-1,4-diene-3,20-dione-17-valerate-21-propionate-21-n-butyl ether, 11β,17α,21,21-tetrahydroxy-16α-methylpregna-1,4-diene-3,20-dione-17-valerate-21-acetate-21-n-hexyl ether, and 11β,17α,21,21-tetrahydroxy-16α-methylpregna-1,4-diene-3,20-dione-17-valerate-21-benzoate-21-methyl ether.

Example 7

In similar manner to the procedures of Examples 1 and 5, using reactants as dictated by the particular steroid 21,21-diester desired, the following compounds are prepared:

6α-fluoro-11β,16α,17α,21,21-pentahydroxypregna-1,4-diene-3,20-dione-16,17-acetonide-21,21-diacetate, 6α-fluoro-11β,16α,17α,21,21-pentahydroxypregna-1,4-diene-3,20-dione-16,17-acetonide-21,21-di-n-butyrate, 6α-fluoro-11β,16α,17α,21,21-pentahydroxypregna-1,4-diene-3,20-dione-16,17-acetonide-21,21-di-n-hexanoate, 6α-fluoro-11β,16α,17α,21,21-pentahydroxypregna-1,4-diene-3,20-dione-16,17-acetonide-21,21-dibenzoate, 6α,9α-difluoro-11β,16α,17α,21,21-pentahydroxypregn-4-ene-3,20-dione-16,17-acetonide-21,21-diacetate, 6α,9α-difluoro-11β,16α,17α,21,21-pentahydroxypregn-4-ene-3,20-dione-16,17-acetonide-21,21-dipropionate, 6α,9α-difluoro-11β,16α,17α,21,21-pentahydroxypregn-4-ene-3,20-dione-16,17-acetonide-21,21-di-n-valerate, 6α,9α-difluoro-11β,16α,17α,21,21-pentahydroxypregn-4-ene-3,20-dione-16,17-acetonide-21,21-di-n-heptanoate, 6α,9α-difluoro-11β,16α,17α,21,21-pentahydroxypregn-4-ene-3,20-dione-16,17-acetonide-21,21-dibenzoate, 6α-fluoro-11β,16α,17α,21,21-pentahydroxypregn-4-ene-3,20-dione-16,17-acetonide-21,21-diacetate, 6α-fluoro-11β,16α,17α,21,21-pentahydroxypregn-4-ene-3,20-dione,16,17-acetonide-21,21-di-n-butyrate, 6α-fluoro-11β,16α,17α,21,21-pentahydroxypregn-4-ene-3,20-dione-16,17-acetonide-21,21-diisovalerate, 6α-fluoro-11β,16α,17α,21,21-pentahydroxypregn-4-ene-3,20-dione-16,17-acetonide-21,21-di-n-heptanoate, 6α-fluoro-11β,16α,17α,21,21-pentahydroxypregn-4-ene-3,20-dione-16,17-acetonide-21,21-dibenzoate, 9α,11β-dichloro-6α-fluoro-16α,17α,21,21-tetrahydroxypregna-1,4-diene-3,20-dione-16,17-acetonide-21,21-diacetate, 9α,11β-dichloro-6α-fluoro-16α,17α,21,21-tetrahydroxypregna-1,4-diene-3,20-dione-16,17-acetonide-21,21-dipropionate, 9α,11β-dichloro-6α-fluoro-16α,17α,21,21-tetrahydroxypregna-1,4-diene-3,20-dione-16,17-acetonide-21,21-di-n-valerate, 9α,11β-dichloro-6α-fluoro-16α,17α,21,21-tetrahydroxypregna-1,4-diene-3,20-dione-16,17-acetonide-21,21-di-n-octanoate, 9α,11β-dichloro-6α-fluoro-16α,17α,21,21-tetrahydroxypregna-1,4-diene-3,20-dione-16,17-acetonide-21,21-di-n-benzoate, 9α-chloro-6α-fluoro-11β,16α,17α,21,21-pentahydroxypregna-1,4-diene-3,20-dione-16,17-acetonide-21,21-diacetate,
9α-chloro-6α-fluoro-11β,16α,17α,21,21-pentahydroxypregna-1,4-diene-3,20-dione-16,17-acetonide-21,21-di-n-butyrate,
9α-chloro-6α-fluoro-11β,16α,17α,21,21-pentahydroxypregna-1,4-diene-3,20-dione-16,17-acetonide-21,21-di-n-hexanoate,
9α-chloro-6α-fluoro-11β,16α,17α,21,21-pentahydroxypregna-1,4-diene-3,20-dione-16,17-acetonide-21,21-di-n-heptanoate,
9α-chloro-6α-fluoro-11β,16α,17α,21,21-pentahydroxypregna-1,4-diene-3,20-dione-16,17-acetonide-21,21-dibenzoate,
6α,9α-difluoro-11β,17α,21,21-tetrahydroxy-16α-methylpregna-1,4-diene-3,20-dione-21,21-diacetate,
6α,9α-difluoro-11β,17α,21,21-tetrahydroxy-16α-methylpregna-1,4-diene-3,20-dione-21,21-dipropionate,
6α,9α-difluoro-11β,17α,21,21-tetrahydroxy-16α-methylpregna-1,4-diene-3,20-dione-21,21-diisovalerate,
6α,9α-difluoro-11β,17α,21,21-tetrahydroxy-16α-methylpregna-1,4-diene-3,20-dione-21,21-di-n-heptanoate,
6α,9α-difluoro-11β, 17α,21,21-tetrahydroxy-16α-methylpregna-1,4-diene-3,20-dione-21,21-dibenzoate,
6α, 9α-difluoro-11β, 17α,21,21-tetrahydroxy-16α-methylpregna-1,4-diene-3,20-dione-17-n-octanoate-21,21-diacetate,
6α,9α-difluoro-11β,17α,21,21-tetrahydroxy-16α-methylpregna-1,4-diene-3,20-dione-17-n-octanoate-21,21-di-n-butyrate,
6α,9α-difluoro-11β,17α,21,21-tetrahydroxy-16α-methylpregna-1,4-diene-3,20-dione-17-n-octanoate-21,21-di-n-hexanoate,
6α,9α-difluoro-11β,17α,21,21-tetrahydroxy-16α-methylpregna-1,4-diene-3,20-dione-17,21,21-tri-n-octanoate,
6α,9α-difluoro-11β,17α,21,21-tetrahydroxy-16α-methylpregna-1,4-diene-3,20-dione-17-n-octanoate-21,21-dibenzoate,
6α,9α-difluoro-11β,17α,21,21-tetrahydroxy-16α-methylpregna-1,4-diene-3,20-dione-17-benzoate-21,21-diformate,
6α,9α-difluoro-11β,17α,21,21-tetrahydroxy-16α-methylpregna-1,4-diene-3,20-dione-17-benzoate-21,21-diacetate,
6α,9α-difluoro-11β,17α,21,21-tetrahydroxy-16α-methylpregna-1,4-diene-3,20-dione-17-benzoate-21,21-dipropionate,
6α,9α-difluoro-11β,17α,21,21-tetrahydroxy-16α-methylpregna-1,4-diene-3,20-dione-17-benzoate-21,21-di-n-butyrate,
6α,9α-difluoro-11β,17α,21,21-tetrahydroxy-16α-methylpregna-1,4-diene-3,20-dione-17-benzoate-21,21-di-n-valerate,
9α-fluoro-11β,17α,21,21-tetrahydroxy-16β-methylpregna-1,4-diene-3,20-dione-17-n-valerate-21,21-diacetate,
9α-fluoro-11β,17α,21,21-tetrahydroxy-16β-methylpregna-1,4-diene-3,20-dione-17-n-valerate-21,21-di-n-butyrate,
9α-fluoro-11β,17α,21,21-tetrahydroxy-16β-methylpregna-1,4-diene-3,20-dione-17-n-valerate-21,21-di-n-heptanoate,
9α-fluoro-11β,17α,21,21-tetrahydroxy-16β-methylpregna-1,4-diene-3,20-dione-17-n-valerate-21,21-di-n-octanoate,
9α-fluoro-11β,17α,21,21-tetrahydroxy-16β-methylpregna-1,4-diene-3,20-dione-17-n-valerate-21,21-dibenzoate,
9α-fluoro-11β,17α,21,21-tetrahydroxy-16β-methylpregn-4-ene-3,20-dione-21,21-diacetate
9α-fluoro-11β,17α,21,21-tetrahydroxy-16β-methylpregn-4-ene-3,20-dione-21,21-dipropionate,
9α-fluoro-11β,17α,21,21-tetrahydroxy-16β-methylpregn-4-ene-3,20-dione-21,21-di-n-valerate,
9α-fluoro-11β,17α,21,21-tetrahydroxy-16β-methylpregn-4-ene-3,20-dione-21,21-di-n-octanoate,
9α-fluoro-11β,17α,21,21-tetrahydroxy-16β-methylpregn-4-ene-3,20-dione-21,21-dibenzoate,
9α-fluoro-11β,16α,17α,21,21-pentahydroxypregna-1,4-diene-3,20-dione-16,17-acetonide-21,21-diacetate,
9α-fluoro-11β,16α,17α,21,21-pentahydroxypregna-1,4-diene-3,20-dione-16,17-acetonide-21,21-dipropionate,
9α-fluoro-11β,16α,17α,21,21-pentahydroxypregna-1,4-diene-3,20-dione-16,17-acetonide-21,21-di-n-butyrate,
9α-fluoro-11β,16α,17α,21,21-pentahydroxypregna-1,4-diene-3,20-dione-16,17-acetonide-21,21-di-n-hexanoate,
9α-fluoro-11β,16α,17α,21,21-pentahydroxypregna-1,4-diene-3,20-dione-16,17-acetonide-21,21-di-n-octanoate,
9α-fluoro-11β,16α,17α,21,21-pentahydroxypregna-1,4-diene-3,20-dione-16,17-acetonide-21,21-dibenzoate,
6α,9α-difluoro-11β,17α,21,21-tetrahydroxy-16α-methylpregna-1,4-diene-3,20-dione-17,21,21-triacetate,
6α,9α-difluoro-11β,17α,21,21-tetrahydroxy-16α-methylpregna-1,4-diene-3,20-dione-17-acetate-21,21-dipropionate,
6α,9α-difluoro-11β,17α,21,21-tetrahydroxy-16α-methylpregna-1,4-diene-3,20-dione-17-acetate-21,21-diisovalerate,
6α,9α-difluoro-11β,17α,21,21-tetrahydroxy-16α-methylpregna-1,4-diene-3,20-dione-17-acetate-21,21-di-n-octanoate,
6α,9α-difluoro-11β,17α,21,21-tetrahydroxy-16α-methylpregna-1,4-diene-3,20-dione-17-acetate-21,21-dibenzoate,
11β,16α,17α,21,21-pentahydroxypregn-4-ene-3,20-dione-16,17-acetonide-21,21-diformate,
11β,16α,17α,21,21-pentahydroxypregn-4-ene-3,20-dione-16,17-acetonide-21,21-diacetate,
11β,16α,17α,21,21-pentahydroxypregn-4-ene-3,20-dione-16,17-acetonide-21,21-di-n-butyrate,
11β,16α,17α,21,21-pentahydroxypregn-4-ene-3,20-dione-16,17-acetonide-21,21-di-n-hexanoate,
11β,16α,17α,21,21-pentahydroxypregn-4-ene-3,20-dione-16,17-acetonide-21,21-dibenzoate,
11β,16α,17α,21,21-pentahydroxypregna-1,4-diene-3,20-dione-16,17-acetonide-21,21-diacetate,
11β,16α,17α,21,21-pentahydroxypregna-1,4-diene-3,20-dione-16,17-acetonide-21,21-dipropionate,
11β,16α,17α,21,21-pentahydroxypregna-1,4-diene-3,20-dione-16,17-acetonide-21,21-di-n-butyrate,
11β,16α,17α,21,21-pentahydroxypregna-1,4-diene-3,20-dione-16,17-acetonide-21,21-di-n-octanoate,
11β,16α,17α,21,21-pentahydroxypregna-1,4-diene-3,20-dione-16,17-acetonide-21,21-dibenzoate, 6α-chloro-11β,16α,17α,21,21-pentahydroxypregn-4-ene-3,20-dione-16,17-acetonide-21,21-diacetate,
6α-chloro-11β,16α,17α,21,21-pentahydroxypregn-4-ene-3,20-dione-16,17-acetonide-21,21-di-n-butyrate,
6α-chloro-11β,16α,17α,21,21-pentahydroxypregn-4-ene-3,20-dione-16,17-acetonide-21,21-diisovalerate,
6α-chloro-11β,16α,17α,21,21-pentahydroxypregn-4-ene-3,20-dione-16,17-acetonide-21,21-di-n-heptanoate,
6α-chloro-11β,16α,17α,21,21-pentahydroxypregn-4-ene-3,20-dione-16,17-acetonide-21,21-dibenzoate,
11β,17α,21,21-tetrahydroxy-16α-methylpregna-1,4-diene-3,20-dione-17-n-valerate-21,21-diacetate,
11β,17α,21,21-tetrahydroxy-16α-methylpregna-1,4-diene-3,20-dione-17-n-valerate-21,21-dipropionate,
11β,17α,21,21-tetrahydroxy-16α-methylpregna-1,4-diene-3,20-dione-17-n-valerate-21,21-di-n-hexanoate,
11β,17α,21,21-tetrahydroxy-16α-methylpregna-1,4-diene-3,20-dione-17-n-valerate-21,21-di-n-octanoate, and
11β,17α,21,21-tetrahydroxy-16α-methylpregna-1,4-diene-3,20-dione-17-n-valerate-21,21-dibenzoate.

What is claimed is:

1. A compound of the formula

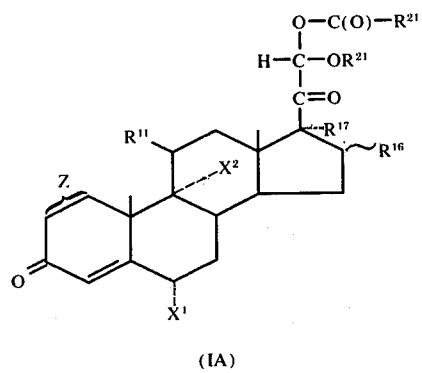

(IA)

wherein $R^{11}$ is chloro or hydroxy; $R^{16}$ independently is methyl; $R^{17}$ independently is hydroxy or acyloxy having 2 to 8 carbon atoms or $R^{16}$ and $R^{17}$ taken together are 16α,17α-isopropylidenedioxy; $R^{21}$ is hydrogen, lower alkyl having 1 to 8 carbon atoms or phenyl; $X^1$ and $X^2$ are independently hydrogen, chloro or fluoro, with the proviso that when $R^{11}$ is chloro, $X^2$ is chloro; $R^{21'}$ is lower alkyl having 1 to 8 carbon atoms; and Z is a single or double bond.

2. A compound of claim 1 wherein the $R^{21}$ and $R^{21'}$ groups contain a total of 1 to 10 carbon atoms.

3. A compound of claim 1 wherein the $R^{21}$ and $R^{21'}$ groups contain a total of 1 to 5 carbon atoms.

4. A compound of the formula

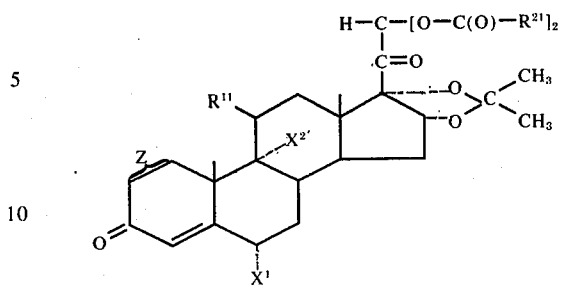

wherein $R^{11}$ is chloro or hydroxy; $R^{21}$ is hydrogen, lower alkyl having 1 to 8 carbon atoms or phenyl; $X^1$ and $X^2$ are independently hydrogen, chloro or fluoro, with the proviso that when $R^{11}$ is chloro, $X^2$ is chloro; and Z is a single or double bond.

5. A compound of claim 4 wherein the $R^{21}$ group contains 0 to 7 carbon atoms.

6. A compound of claim 4 wherein the $R^{21}$ group contains 0 to 4 carbon atoms.

7. A compound of claim 1 of the formula

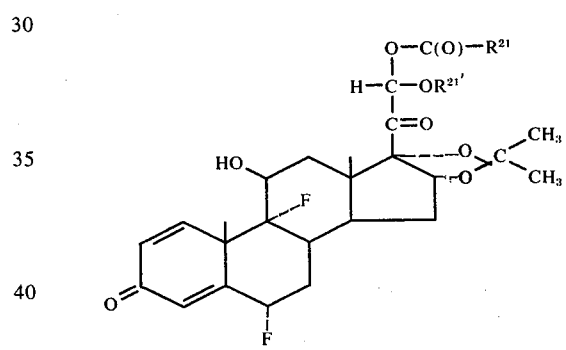

wherein $R^{21}$ and $R^{21'}$ are as defined in claim 1.

8. The compound of claim 7 which is 6α,9α-difluoro-11β,16α,17α,21,21-pentahydroxypregna-1,4-diene-3,20-dione-16,17-acetonide-21-acetate-21-methyl ether.

9. The compound of claim 7 which is 6α,9α-difluoro-11β,16α,17α,21,21-pentahydroxypregna-1,4-diene-3,20-dione-16,17-acetonide-21-acetate-21-n-amyl ether.

10. The compound of claim 7 which is 6α,9α-difluoro-11β,16α,17α,21,21pentahydroxypregna-1,4-diene-3,20-dione-16,17-acetonide-21-acetate-21-isopropyl ether, 11. The compound of claim 7 which is 6α,9α-difluoro-11β,16α,17α,21,21-pentahydroxypregna-1,4-diene-3,20-dione-16,17-acetonide-21-isovalerate-21-methyl ether.

12. A compound of claim 4 of the formula

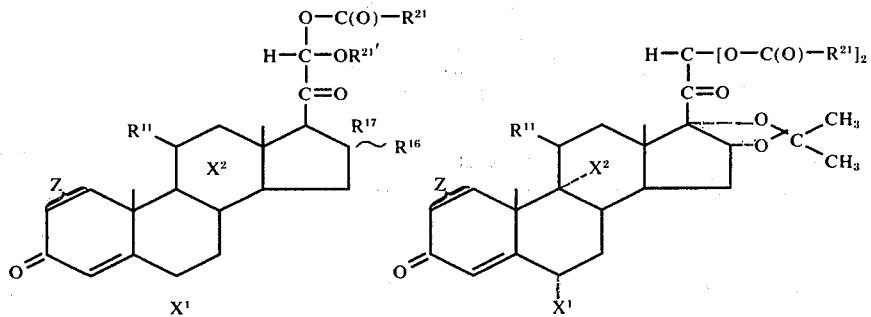

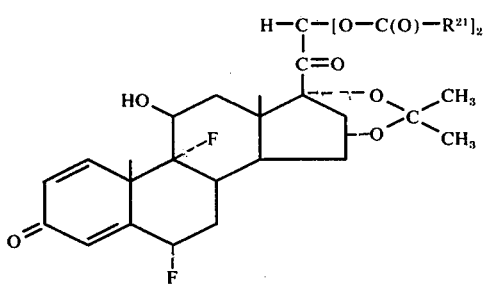

wherein $R^{11}$ is chloro or hydroxy; $R^{16}$ independently is methyl; $R^{17}$ independently is hydroxy or acyloxy having 2 to 8 carbon atoms or $R^{16}$ and $R^{17}$ taken together are 16α,17α-isopropylidenedioxy; $R^{21}$ is hydrogen, lower alkyl having 1 to 8 carbon atoms or phenyl; $X^1$ and $X^2$ are independently hydrogen, chloro or fluoro, with the proviso that when $R^{11}$ is chloro, $X^2$ is chloro; $R^{21\prime}$ is lower alkyl having 1 to 8 carbon atoms; and z is a single or double bond.

16. A method for relieving symptoms associated with inflammatory disorders comprising administering an effective amount of a compound selected from the group represented by the formulas:

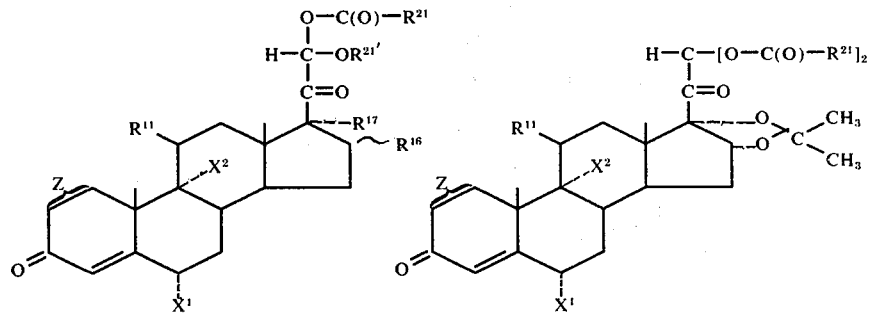

wherein $R^{21}$ is as defined in claim 4.

13. The compound of claim 12 which is 6α,9α-difluoro-11β,16α,17α,21,21-pentahydroxypregna-1,4-diene-3,20-dione-16,17-acetonide-21,21-diacetate.

14. The compound of claim 12 which is 6α,9α-difluoro-11β,16α,17α,21,21-pentahydroxypregna-1,4-diene-3,20-dione-16,17-acetonide-21,21-dipropionate.

15. A pharmaceutical composition useful for treating inflammatory disorders comprising a pharmaceutically acceptable nontoxic carrier in admixture with an effective amount of a compound selected from the group represented by the formulas:

wherein $R^{11}$ is chloro or hydroxy; $R^{16}$ independently is methyl; $R^{17}$ independently is hydroxy or acyloxy having 2 to 8 carbon atoms or $R^{16}$ and $R^{17}$ taken together are 16α,17α-isopropylidenedioxy; $R^{21}$ is hydrogen, lower alkyl having 1 to 8 carbon atoms or phenyl; $X^1$ and $X^2$ are independently hydrogen, chloro or fluoro, with the proviso that when $R^{11}$ is chloro, $X^2$ is chloro; $R^{21\prime}$ is lower alkyl having 1 to 8 carbon atoms; and Z is a single or double bond; or a pharmaceutically acceptable composition containing same.

17. A process for preparing a compound selected from the group represented by the formulas:

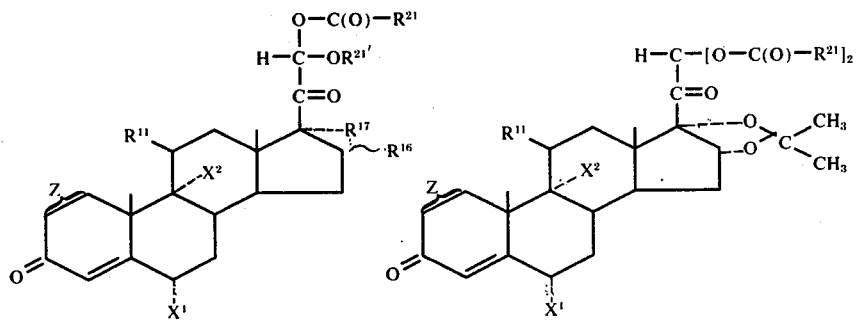

a. acylating a 21-aldehyde-hemiacetal having the formula

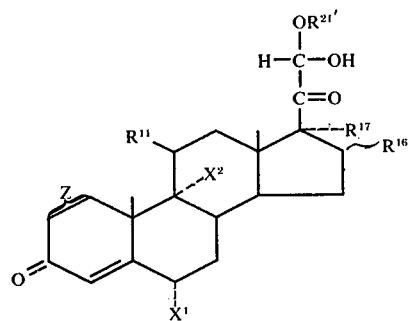

wherein $R^{11}$, $R^{16}$, $R^{17}$, $R^{21'}$, $X^1$, $X^2$ and Z are as previously defined, to obtain a 21-ester-21-alkyl ether; or b. acylating a 21-aldehyde hydrate of the formula

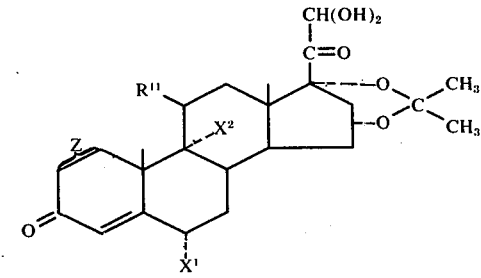

wherein $R^{11}$, $X^1$, $X^2$ and Z are as previously defined to obtain a 21,21-diester.

wherein $R^{11}$ is chloro or hydroxy; $R^{16}$ independently is methyl; $R^{17}$ independently is hydroxy or acyloxy having 2 to 8 carbon atoms or $R^{16}$ and $R^{17}$ taken together are 16α,17α-isopropylidenedioxy; $R^{21}$ is hydrogen, lower alkyl having 1 to 8 carbon atoms or phenyl; $X^1$ and $X^2$ are independently hydrogen, chloro or fluoro, with the proviso that when $R^{11}$ is chloro, $X^2$ is chloro; $R^{21'}$ is lower alkyl having 1 to 8 carbon atoms; and Z is a single or double bond, which process comprises:

* * * * *

UNITED STATES PATENT AND TRADEMARK OFFICE
CERTIFICATE OF CORRECTION

PATENT NO. : 3,996,358
DATED : December 7, 1976
INVENTOR(S) : MICHAEL MARX and DENIS JOHN KERTESZ It is certified that error appears in the above-identified patent and that said Letters Patent are hereby corrected as shown below:

Column 1, line 33, $-O-CO(O)-R^{21}$ should read -- $-O-C(O)-R^{21}$ --. Column 2, line 36, "16 to 24 atoms" should read -- 16 to 24 carbon atoms --. Column 2, line 67 "0 tp" should read -- 0 to --. Column 3, line 12, "The wavy line ( )" should read -- The wavy line (∿)" --. Column 5, line 37, "ahydride" should read -- anhydride --. Column 6, lines 10 and 11, "6α,9α-difluoro-11β,17α,1-7α,21-tetrahydroxypregna" should read -- 6α,9α-difluro-11β,16α,17α,21-tetrahydroxypregna --. Column 9, line 4, "α,9α- difluoro" should read -- 6α,9α-difluoro --.

UNITED STATES PATENT OFFICE
CERTIFICATE OF CORRECTION

Patent No. 3,996,358          Dated December 7, 1976

Inventor(s) Michael Marx et al.

It is certified that error appears in the above-identified patent and that said Letters Patent are hereby corrected as shown below:

Column 17, Claim 1, lines 35 to 50 that portion of the formula reading

" 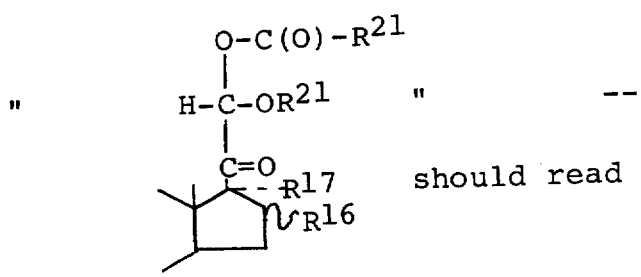 should read -- 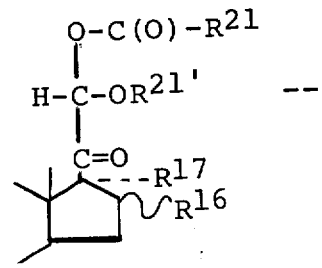 --

UNITED STATES PATENT OFFICE
CERTIFICATE OF CORRECTION

Patent No. 3,996,358        Dated December 7, 1976

Inventor(s) Michael Marx et al.

It is certified that error appears in the above-identified patent and that said Letters Patent are hereby corrected as shown below:

Column 19 and 20, Claim 15 lines 1 to 19 that portion of the formula reading

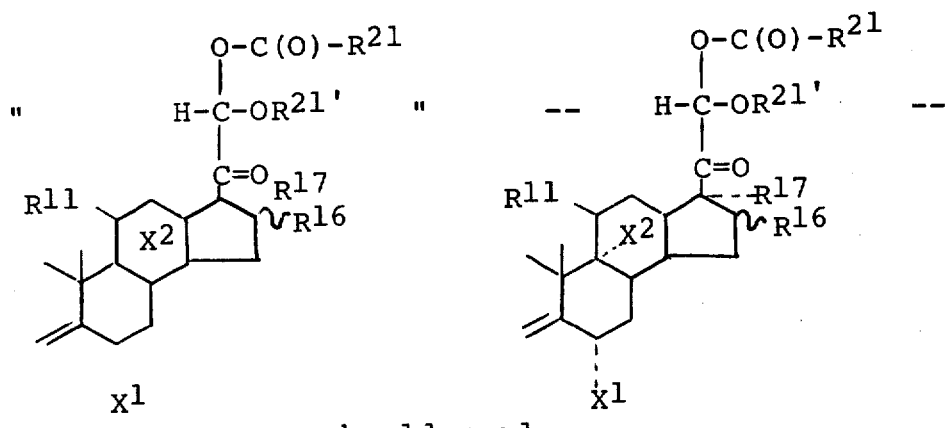

should read

Signed and Sealed this

Seventeenth Day of May 1977

[SEAL]

Attest:

RUTH C. MASON
*Attesting Officer*

C. MARSHALL DANN
*Commissioner of Patents and Trademarks*